United States Patent
Wang et al.

(10) Patent No.: US 11,400,199 B2
(45) Date of Patent: Aug. 2, 2022

(54) BIOARTIFICIAL LIVER BASED ON HUMAN IPSCS-DERIVED HEPATOCYTE-LIKE CELLS AND MULTILAYER POROUS BIOREACTOR

(71) Applicant: Nanjing Drum Tower Hospital, Nanjing (CN)

(72) Inventors: Jinglin Wang, Nanjing (CN); Haozhen Ren, Nanjing (CN); Yitao Ding, Nanjing (CN); Xiaolei Shi, Nanjing (CN)

(73) Assignee: NANJING DRUM TOWER HOSPITAL, Nanjing (CN)

(*) Notice: Subject to any disclaimer, the term of this patent is extended or adjusted under 35 U.S.C. 154(b) by 0 days.

(21) Appl. No.: 17/434,766

(22) PCT Filed: Feb. 7, 2021

(86) PCT No.: PCT/CN2021/075804
§ 371 (c)(1),
(2) Date: Aug. 30, 2021

(87) PCT Pub. No.: WO2021/184999
PCT Pub. Date: Sep. 23, 2021

(65) Prior Publication Data
US 2022/0143293 A1    May 12, 2022

(30) Foreign Application Priority Data
Mar. 16, 2020   (CN) .......................... 202010182402.3

(51) Int. Cl.
*A61M 1/36*   (2006.01)
*A61M 1/16*   (2006.01)
(Continued)

(52) U.S. Cl.
CPC ........ *A61M 1/3689* (2014.02); *A61M 1/1629* (2014.02); *A61M 1/1698* (2013.01);
(Continued)

(58) Field of Classification Search
CPC .............. A61M 1/3689; A61M 1/1629; A61M 1/1698; A61M 1/267; A61M 1/3489; A61M 1/3639; A61M 1/3672
See application file for complete search history.

(56) References Cited

U.S. PATENT DOCUMENTS 5,981,211 A * 11/1999 Hu .................... C12M 25/12
435/813
11,096,388 B2 * 8/2021 Paun ................... C12M 29/10
(Continued)

FOREIGN PATENT DOCUMENTS

CN          101381678 A      3/2009
CN          101559246 A  * 10/2009
(Continued)

OTHER PUBLICATIONS

Chenxia Hu, et al., In vitro culture of isolated primary hepatocytes and stem cell-derived hepatocyte-like cells for liver regeneration, Protein Cell, 2015, pp. 562-574, 6(8).

*Primary Examiner* — Krishnan S Menon
(74) *Attorney, Agent, or Firm* — Bayramoglu Law Offices LLC

(57) ABSTRACT

A bioartificial liver (BAL) based on human induced pluripotent stem cells (iPSCs)-derived hepatocyte-like cells (HLCs) and a multilayer porous bioreactor is provided. The plasma separation/retransfusion loop part includes a blood input pipe, an exhaust pipe spring clamp, a blood input peristaltic pump, a heparin pump, a plasma separation column, a first pressure monitor, and a heater. The cell reactor/plasma component exchange double-loop part includes a plasma input peristaltic pump, and a semipermeable membrane exchange column, a plasma exchange peristaltic pump, a red blood cell (RBC) pool, a membrane lung, a multilayer porous bioreactor, a second pressure monitor, and a third pressure monitor arranged in a 37° C. dedicated incubator. An outlet of the third pressure monitor and a blood cell outlet are connected to an inlet of the first pressure monitor, and then connected to the heater and a blood output pipe in sequence.

7 Claims, 2 Drawing Sheets

(51) Int. Cl.
     *A61M 1/26*     (2006.01)
     *A61M 1/34*     (2006.01)

(52) U.S. Cl.
     CPC .......... *A61M 1/267* (2014.02); *A61M 1/3489* (2014.02); *A61M 1/3639* (2013.01); *A61M 1/3672* (2013.01)

(56) References Cited

U.S. PATENT DOCUMENTS

| | | | | |
|---|---|---|---|---|
| 2011/0125286 A1* | 5/2011 | Selden | ................... | C12M 25/16 |
| | | | | 435/284.1 |
| 2011/0313540 A1* | 12/2011 | Selden | ................ | A61M 1/3472 |
| | | | | 623/23.65 |
| 2012/0111795 A1* | 5/2012 | Chamuleau | ............ | C12M 29/00 |
| | | | | 435/370 |
| 2013/0085077 A1* | 4/2013 | Croce | ................ | C12N 15/1137 |
| | | | | 435/6.12 |

FOREIGN PATENT DOCUMENTS

| | | | |
|---|---|---|---|
| CN | 101559246 | A | 10/2009 |
| CN | 102250766 | A | 11/2011 |
| CN | 103877631 | A | 6/2014 |
| CN | 104225698 | A | 12/2014 |
| CN | 106075625 | A | 11/2016 |
| CN | 207445274 | U | 6/2018 |
| CN | 108421106 | A | 8/2018 |
| CN | 108485965 | A | 9/2018 |
| CN | 110448749 | A | 11/2019 |
| CN | 110478548 | A | 11/2019 |
| CN | 111249552 | A | 6/2020 |
| EP | 2168614 | A1 | 3/2010 |

\* cited by examiner

BIOARTIFICIAL LIVER BASED ON HUMAN IPSCS-DERIVED HEPATOCYTE-LIKE CELLS AND MULTILAYER POROUS BIOREACTOR

CROSS REFERENCE TO THE RELATED APPLICATIONS

This application is the national phase entry of International Application No. PCT/CN2021/075804, filed on Feb. 7, 2021, which is based upon and claims priority to Chinese Patent Application No. 202010182402.3, filed on Mar. 16, 2020, the entire contents of which are incorporated herein by reference.

TECHNICAL FIELD

The present disclosure relates to the technical field of bioartificial livers (BALs), and in particular to a BAL based on induced pluripotent stem cells (iPSCs)-derived hepatocyte-like cells (HLCs) and a multilayer porous bioreactor.

BACKGROUND

BAL is a novel liver support system that uses human or animal-derived hepatocytes to temporarily or partially replace a failed liver function in the body, which can assist in the treatment of liver failure or related liver diseases. BAL not only has the detoxification function of the liver, but also can achieve the synthesis, metabolism, secretion, and other functions of the liver through hepatocytes in a reactor, which is expected to fundamentally replace the functions of the liver. In recent years, great progress has been made in the BAL research, and it has shown that BAL has a liver support effect. Human liver cancer cell lines, such as the C3A cell line, have been used in the BAL system (extracorporeal liver assist device (ELAD)) in the United States, which have the defect of poor metabolic function, and experiments have proved that the cell line HepG2 where C3A is derived actually shows no therapeutic effect on acute liver failure (ALF) mice. Pig-derived primary hepatocytes have also been used in the Academic Medical Center-BAL (AMC-BAL) and HepatAssist systems abroad, and these cell sources have been criticized for immunogenicity (anti-pig IgG is found in the body after clinical application) and have the risk of animal-derived virus infection. However, in order to fully achieve the role of extracorporeal liver support and replacement and meet the needs of clinical treatment, many problems still need to be solved. Therefore, how to establish an efficient and safe BAL support system and acquire functional hepatocytes are problems that urgently need to be solved in clinical practice.

SUMMARY

In view of the above-mentioned shortcomings in the prior art, the technical problem to be solved by the present disclosure is to provide a BAL based on iPSCs-derived HLCs and a multilayer porous bioreactor, which can effectively reduce the risk of xenogeneic virus infection and immune response.

In order to achieve the above technical objective, the present disclosure adopts the following technical solutions. A BAL based on human iPSCs-derived HLCs and a multilayer porous bioreactor includes a plasma separation/retransfusion loop part and a cell reactor/plasma component exchange double-loop part that are connected to each other via connecting lines.

The plasma separation/retransfusion loop part includes a blood input pipe, a blood input peristaltic pump, a heparin pump, a plasma separation column, a first pressure monitor, and a heater that are connected in sequence via connecting lines. An exhaust pipe spring clamp is arranged on a connecting line between the blood input pipe and the blood input peristaltic pump; a blood inlet, a plasma outlet, and a blood cell outlet are arranged on the plasma separation column; and the blood inlet communicates with an outlet of the heparin pump.

The cell reactor/plasma component exchange double-loop part includes a plasma input peristaltic pump, and a semipermeable membrane exchange column, a plasma exchange peristaltic pump, a red blood cell (RBC) pool, a membrane lung, the multilayer porous bioreactor, a second pressure monitor, and a third pressure monitor arranged in a 37° C. dedicated incubator, which are connected to the plasma outlet in sequence via connecting lines. A lower plasma inlet, a lower plasma outlet, an upper plasma inlet, and an upper plasma outlet are arranged on the semipermeable membrane exchange column; the lower plasma inlet communicates with an outlet of the plasma input peristaltic pump, and the lower plasma outlet communicates with an inlet of the plasma exchange peristaltic pump. The iPSCs-derived HLCs are perfused into the multilayer porous bioreactor; the second pressure monitor communicates with the upper plasma inlet, and the upper plasma outlet communicates with the third pressure monitor. An outlet of the third pressure monitor and the blood cell outlet are connected to an inlet of the first pressure monitor; and an outlet of the first pressure monitor is connected to the heater and a blood output pipe in sequence.

Further, the plasma separation column is a membrane plasma separator.

Further, the semipermeable membrane exchange column is a membrane plasma component separator, and a semipermeable membrane has a pore size of 11 nm.

Further, the RBC pool is a silicone rubber bag with 110 mL of RBCs; an inlet and an outlet is arranged at front and rear ends of the silicone rubber bag, respectively; and the inlet and the outlet is connected to connecting lines.

Further, the membrane lung is a membrane oxygenator.

Further, the connecting lines are made of medical grade polyvinyl chloride (PVC); and connecting lines connected to the blood input peristaltic pump and the plasma input peristaltic pump have an outer diameter of 13 mm, and other connecting lines have an outer diameter of 5.7 mm.

Further, the multilayer porous bioreactor includes a tank body, a tank cover, and a multilayer porous plate device. The tank cover is threadedly connected to an upper tank mouth of the tank body, and further sealed by a rubber ring sleeved on the upper tank mouth. A cell input hole and a culture outlet pipe are arranged on an upper surface of the tank cover; and a culture inlet pipe is arranged at the bottom of the tank body. The human iPSCs-derived HLCs are perfused into the tank body through the cell input hole. The cell input hole is equipped with a sealing cover. The membrane lung communicates with the culture inlet pipe via a connecting line; the second pressure monitor communicates with the culture outlet pipe via a connecting line; and the multilayer porous plate device is connected to an inner wall of the tank body in a manner such that the multilayer porous plate device can slide up and down.

Further, the multilayer porous plate device includes at least one layer of a porous plate, and the porous plate includes a plate, grooves, and bottom brackets. The grooves and the bottom brackets are circularly arranged on an upper surface and a lower surface of the plate at opposite positions, respectively. Upper and lower adjacent layers of porous plates are removably connected by inserting the bottom brackets of the upper porous plate into the grooves of the lower porous plate. Vertical hollowing holes are evenly distributed on a surface of the plate, and the vertical hollowing holes penetrate through the plate longitudinally. The bottom brackets are hollow cylinders; and horizontal hollowing holes are arranged on side walls of the bottom brackets.

Further, the tank body has a diameter of 126 mm, a height of 160 mm, and a wall thickness of 4 mm; the multilayer porous plate device includes 50 to 60 layers of porous plates; circular polycarbonate (PC) plates with a diameter of 120 mm and a thickness of 1 mm are used as the plates of the porous plates; and an outer surface of the circular PC plate is coated with a layer of growth factor and collagen.

Further, the grooves and the bottom brackets are circularly arranged respectively on the upper surface and the lower surface of the plate correspondingly in an inner ring and an outer ring, with 6, 8, or 11 grooves and bottom brackets in each ring; and the grooves and the bottom brackets are evenly distributed on a circumference around a center of the plate. The grooves are cylindrical grooves with a diameter of 11 mm and a depth of 0.8 mm; the bottom brackets are annular bottom brackets with a diameter of 11 mm and a height of 2 mm; and the vertical hollowing holes and the horizontal hollowing holes are circular holes with a diameter of 2 mm.

Compared with the prior art, the present disclosure has the following advantages.

1) The present disclosure controls a blood flow in BAL at 37° C. through a 37° C. dedicated incubator to maintain the temperature required for the optimal state of blood and cells, and provides oxygen required by cells through an RBC pool and a membrane lung, thereby ensuring the temperature and oxygen supply required by blood and cells to provide the efficiency of BAL.

2) The present disclosure uses human-derived cells (human iPSCs-derived HLCs) to reduce the risk of xenogeneic virus infection.

3) In the present disclosure, the number of layers in the multilayer porous bioreactor can be adjusted to effectively adjust the number of cells and increase the effective exchange area, and horizontal hollowing holes on the bottom brackets allow a flowing liquid to uniformly contact with cells radially, which reduces the cell damage caused by flow rate, improves the liquid exchange efficiency, and enables adequate material exchange. The outer surface of the PC plate is coated with growth factor and collagen to reduce the shear force, promote the cell adhesion and 3D aggregation growth, and improve the biocompatibility. A liquid flows in reverse from bottom to top in the multilayer porous bioreactor, which promotes the liquid exchange efficiency. Meanwhile, the tank body has a large volume and can carry a large number of cells, which can meet clinical demands.

4) In the present disclosure, the material exchange is achieved through a semipermeable membrane exchange column, which effectively reduces the risk of immune response.

Figure 1:
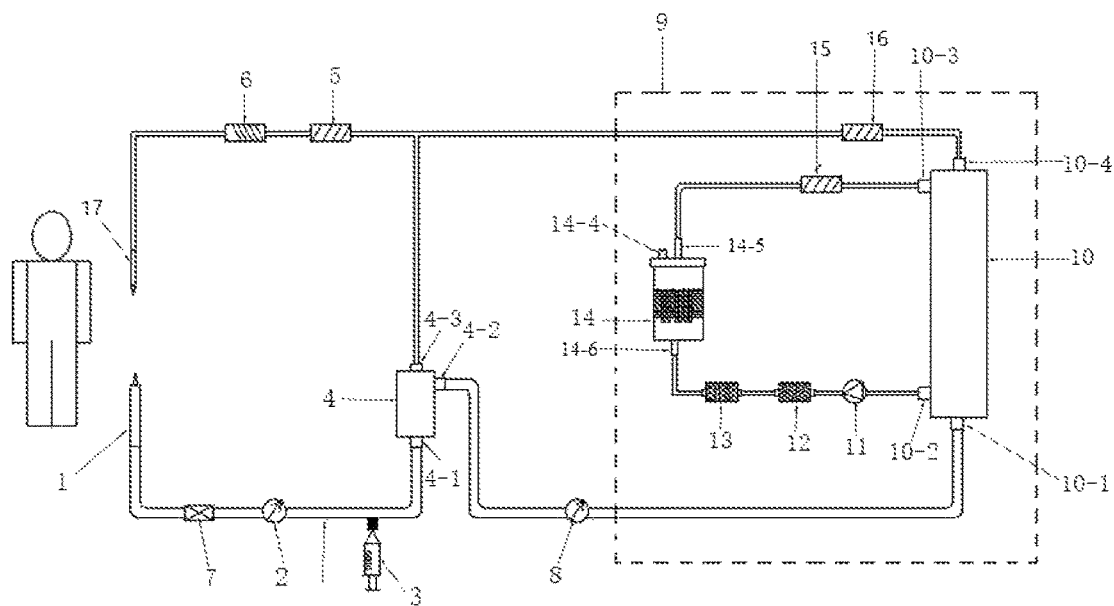
FIG. 1 is a schematic diagram illustrating an overall structure of the BAL of the present disclosure.

Reference numerals: blood input pipe 1; blood input peristaltic pump 2; heparin pump 3; plasma separation column 4; blood inlet 4-1; plasma outlet 4-2; blood cell outlet 4-3; first pressure monitor 5; heater 6; exhaust pipe spring clamp 7; plasma input peristaltic pump 8; 37° C. dedicated incubator 9; semipermeable membrane exchange column 10; lower plasma inlet 10-1; lower plasma outlet 10-2; upper plasma inlet 10-3; upper plasma outlet 10-4; plasma exchange peristaltic pump 11; RBC pool 12; membrane lung 13; multilayer porous bioreactor 14; tank body 14-1; tank cover 14-2; multilayer porous plate device 14-3; plate 14-31; groove 14-32; bottom bracket 14-33; vertical hollowing hole 14-34; horizontal hollowing hole 14-35; growth factor and collagen 14-36; cell input hole 14-4; culture outlet pipe 14-5; culture inlet pipe 14-6; second pressure monitor 15; third pressure monitor 16; and blood output pipe 17.

DETAILED DESCRIPTION THE EMBODIMENTS

To enable a person skilled in the art to better understand the technical solutions of the present disclosure, the embodiments of the present disclosure are further described in detail below with reference to the accompanying drawings.

Figure 2:
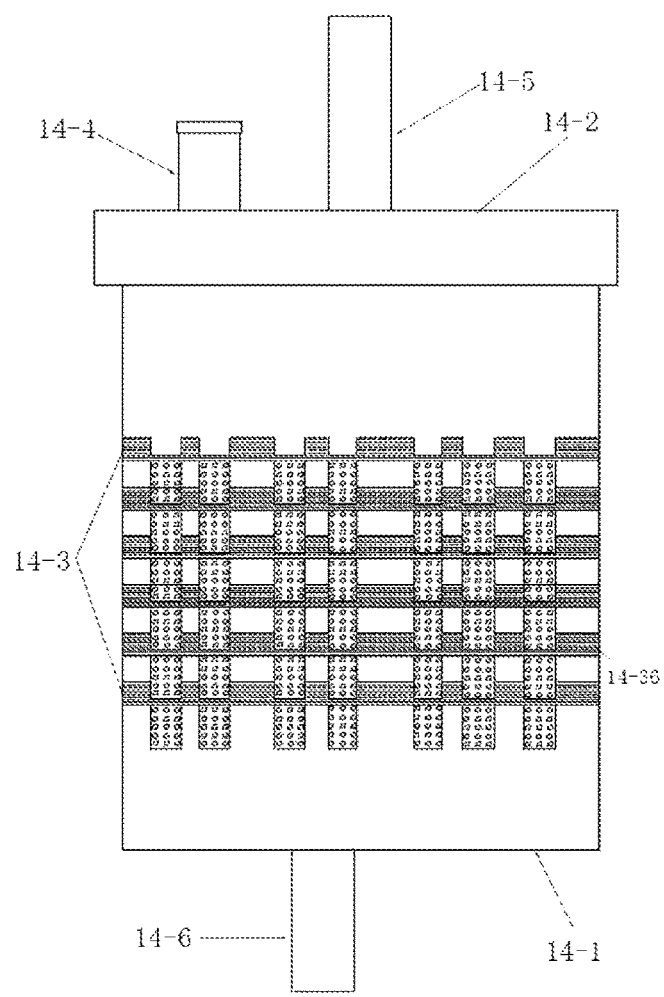
FIG. 2 is a schematic diagram illustrating a structure of the multilayer porous bioreactor in FIG. 1.
Figure 3:
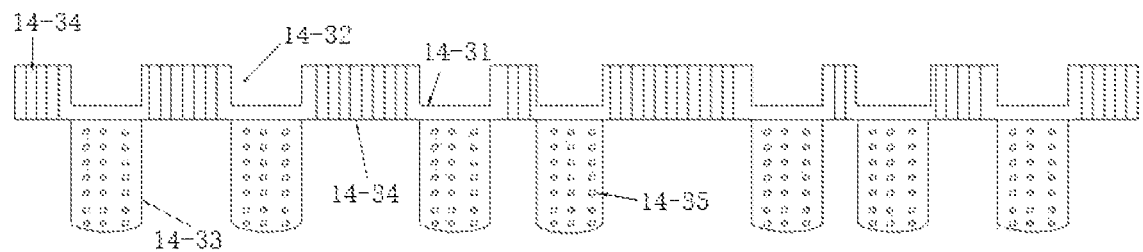
FIG. 3 is a side view of a porous plate of the multilayer porous plate device in FIG. 2.
Figure 4:
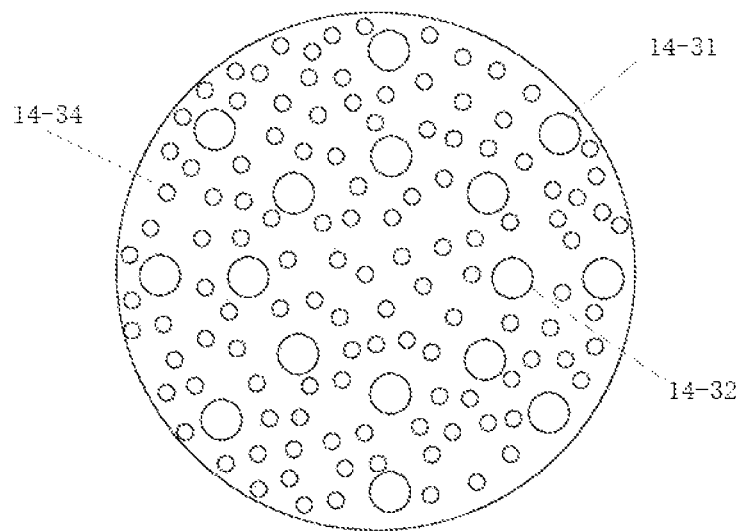
FIG. 4 is a top view of the porous plate in FIG. 3.

As shown in FIG. 1 to FIG. 4, a BAL based on human iPSCs-derived HLCs and a multilayer porous bioreactor is provided, including a plasma separation/retransfusion loop part and a cell reactor/plasma component exchange double-loop part that are connected to each other via connecting lines. The connecting lines are made of medical grade PVC.

The plasma separation/retransfusion loop part includes the blood input pipe 1, the blood input peristaltic pump 2, the heparin pump 3, the plasma separation column 4, the first pressure monitor 5, and the heater 6 that are connected in sequence via connecting lines. The exhaust pipe spring clamp 7 is arranged on a connecting line between the blood input pipe 1 and the blood input peristaltic pump 2. The plasma separation column 4 is a membrane plasma separator (which can be purchased from Asahi Kasei Kuraray Medical Co., Ltd.); the blood inlet 4-1, the plasma outlet 4-2, and the blood cell outlet 4-3 are arranged on the plasma separation column 4; and the blood inlet 4-1 communicates with an outlet of the heparin pump 3.

The cell reactor/plasma component exchange double-loop part includes the plasma input peristaltic pump 8, and the semipermeable membrane exchange column 10, the plasma exchange peristaltic pump 11, the RBC pool 12, the membrane lung 13, the multilayer porous bioreactor 14, the second pressure monitor 15, and the third pressure monitor 16 arranged in the 37° C. dedicated incubator 9, which are connected to the plasma outlet 4-2 in sequence via connecting lines. Connecting lines connected to the blood input peristaltic pump 2 and the plasma input peristaltic pump 8 have an outer diameter of 13 mm, and other connecting lines have an outer diameter of 5.7 mm. The semipermeable membrane exchange column 10 is a membrane plasma component separator, and a semipermeable membrane has a pore size of 11 nm (which can be purchased from Kawasumi Laboratories). The lower plasma inlet 10-1, the lower plasma outlet 10-2, the upper plasma inlet 10-3, and the upper plasma outlet 10-4 are arranged on the semipermeable membrane exchange column 10; and the lower plasma inlet 10-1 communicates with an outlet of the plasma input peristaltic pump 8, and the lower plasma outlet 10-2 communicates with an inlet of the plasma exchange peristaltic pump 11. The RBC pool 12 is a silicone rubber bag with 110 mL of RBCs, and an inlet and an outlet are arranged at front and rear ends of the silicone rubber bag, respectively. An outlet of the plasma exchange peristaltic pump 11 communicates with the inlet of the RBC pool 12 via a connecting line. The membrane lung 13 is a membrane oxygenator (which can be purchased from WEGO), and the outlet of the RBC pool 12 communicates with an inlet of the membrane lung 13 via a connecting line. The multilayer porous bioreactor 14 includes the tank body 14-1, the tank cover 14-2, and the multilayer porous plate device 14-3. The tank body 14-1 has a diameter of 126 mm, a height of 160 mm, and a wall thickness of 4 mm; the tank cover 14-2 is threadedly connected to an upper tank mouth of the tank body 14-1, and further sealed by a rubber ring sleeved on the upper tank mouth. The multilayer porous plate device 14-3 is connected to an inner wall of the tank body 14-1 in a manner such that the multilayer porous plate device can slide up and down (similar to a connection relationship between a press plate and an inner wall of a washing tub). The cell input hole 14-4 and the culture outlet pipe 14-5 are arranged on an upper surface of the tank cover 14-2, and the culture inlet pipe 14-6 is arranged at the bottom of the tank body 14-1. The human iPSCs-derived HLCs are perfused into the tank body 14-1 through the cell input hole 14-4. The cell input hole 14-4 is equipped with a sealing cover. The membrane lung 13 communicates with the culture inlet pipe 14-6 via a connecting line. The second pressure monitor 15 communicates with the culture outlet pipe 14-5 via a connecting line. The multilayer porous plate device 14-3 is connected to an inner wall of the tank body 14-1 in a manner such that the multilayer porous plate device can slide up and down (similar to a connection relationship between a press plate and an inner wall of a washing tub). One end of the second pressure monitor 15 is connected to the culture outlet pipe 14-5 via a connecting line, and the other end of the second pressure monitor 15 is connected to the upper plasma inlet 10-3 via a connecting line. The upper plasma outlet 10-4 communicates with the third pressure monitor 16; an outlet of the third pressure monitor 16 and the blood cell outlet 4-3 are connected to an inlet of the first pressure monitor 5; and an outlet of the first pressure monitor 5 is connected to the heater 6 and the blood output pipe 17 in sequence, and finally communicates with the human body.

In an embodiment, the multilayer porous plate device 14-3 includes at least one layer of a porous plate, and the porous plate includes the plate 14-31, the grooves 14-32, and the bottom brackets 14-33. The grooves 14-32 and the bottom brackets 14-33 are circularly arranged on an upper surface and a lower surface of the plate 14-31 at opposite positions, respectively. Upper and lower adjacent layers of porous plates are removably connected by inserting the bottom brackets 14-33 of the upper porous plate into the grooves 14-32 of the lower porous plate. Vertical hollowing holes 14-34 are evenly distributed on a surface of the plate 14-31, and the vertical hollowing holes 14-34 penetrate through the plate 14-31 longitudinally; the bottom brackets 14-33 are hollow cylinders; and horizontal hollowing holes 14-35 are arranged on side walls of the bottom brackets 14-33.

Further, the multilayer porous plate device 14-3 is composed of 50 to 60 layers of porous plates; circular PC plates with a diameter of 120 mm and a thickness of 1 mm are used as the plates 14-31 of the porous plates; and an outer surface of the circular PC plate is coated with a layer of growth factor and collagen 14-36.

Further, the grooves 14-32 and the bottom brackets 14-33 are circularly arranged respectively on the upper surface and the lower surface of the plate 14-31 correspondingly in an inner ring and an outer ring, with 6, 8, or 11 grooves 14-32 and bottom brackets 14-33 in each ring; and the grooves 14-32 and the bottom brackets 14-33 are evenly distributed on a circumference around a center of the plate 14-31. The grooves 14-32 are cylindrical grooves with a diameter of 11 mm and a depth of 0.8 mm; the bottom brackets 14-33 are annular bottom brackets with a diameter of 11 mm and a height of 2 mm; and the vertical hollowing holes 14-34 and the horizontal hollowing holes 14-35 are circular holes with a diameter of 2 mm.

When the BAL based on human iPSCs-derived HLCs and a multilayer porous bioreactor of the present disclosure is used, the human iPSCs-derived HLCs are slowly perfused into the tank body 14-1 aseptically through the cell input hole 14-4 of the multilayer porous bioreactor 14, then the 37° C. dedicated incubator 9 is turned on to cultivate the cells for 4 h until the cells are stably adhered; the blood of a patient is drawn out and then enters the BAL system through the blood input pipe 1; the plasma separation column 4 separates blood cells in the blood from plasma, and separated plasma enters the 37° C. dedicated incubator 9 through the plasma input peristaltic pump 8 to communicate with the semipermeable membrane exchange column 10; and the plasma in the semipermeable membrane exchange column 10 is passed through the RBC pool 12 and the membrane lung 13 through the plasma exchange peristaltic pump 11, and enters the multilayer porous bioreactor 14 through the culture inlet pipe 14-6. The multilayer porous plate device 14-3 is preferably composed of 50 to 60 layers of porous plates, and the number of layers is adjustable. Liquid can flow radially around the plate 14-31 through the horizontal hollowing holes 14-35 on the side walls of the bottom brackets 14-33 at each layer, which allows full liquid exchange. The plate 14-31 is a circular PC plate that has prominent biocompatibility with human iPSCs-derived HLCs, and an outer surface of the plate is coated with a layer of growth factor and collagen 14-36, which is conducive to the cell aggregation and adhesion, 3D cultivation, and full function display, such that toxic substances in the plasma can be effectively exchanged with the active ingredients in the multilayer porous bioreactor 14. The culture outlet pipe 14-5 of the multilayer porous bioreactor 14 is connected to the second pressure monitor 15, such that a circulating liquid can be transferred to the semipermeable membrane exchange column 10 through the upper plasma inlet 10-3. The upper plasma outlet 10-4 of the semipermeable membrane exchange column 10 is connected to the third pressure monitor 16, such that the circulating liquid exits the 37° C. dedicated incubator 9, and is combined with blood cells output from the blood cell outlet 4-3 of the plasma separation column 4, then passed through the first pressure monitor 5 and the heater 6, and finally re-transfused into the human body through the blood output pipe 17.

In the BAL based on human iPSCs-derived HLCs and a multilayer porous bioreactor of the present disclosure, human-derived cells are adopted, which avoids xenogeneic virus infection, significantly improves biocompatibility, promotes 3D cell cultivation, and gives full play to cell functions similar to that at in vivo cultivation (after cultivation, albumin secretion is maintained at 70 μg/116 cells/day, an ammonia clearance rate is maintained at 25 μmol/116 cells/ day, a urea synthesis rate is maintained at 10 μg/116 cells/day, and a glucose metabolism rate is maintained at 120 μmol/116 cells/day). A flowing liquid uniformly contacts cells radially, which reduces the cell damage caused by flow rate, improves the liquid exchange efficiency, and enables adequate material exchange. Moreover, the tank body has a large volume and can carry a large number of cells, which can meet clinical demands (a cell carrying capacity reaches 1,111). A semipermeable membrane of the semipermeable membrane exchange column 10 is used for material exchange, which effectively reduces the immune response (the semipermeable membrane has a pore size of 11 nm; and no viruses such as HBV and HIV have been detected, and the levels of IgG and IgM immune antibodies have not been significantly increased or decreased, indicating prominent virus and immune safety). The 37° C. dedicated incubator 9, the RBC pool 12, and the membrane lung 13 can ensure the temperature and oxygen supply required by blood and cells to provide the efficiency of BAL.

The above are only preferred implementations of the present disclosure, and the protection scope of the present disclosure is not limited thereto. All technical solutions based on the idea of the present disclosure should fall within the protection scope of the present disclosure. It should be noted that, for a person of ordinary skill in the art, several improvements and modifications may be made without departing from the principle of the present disclosure, which should be deemed as falling within the protection scope of the present disclosure.

What is claimed is:

1. A bioartificial liver (BAL) based on human induced pluripotent stem cells (iPSCs)-derived hepatocyte-like cells (HLCs) and a multilayer porous bioreactor, comprising a plasma separation/retransfusion loop part and a cell reactor/plasma component exchange double-loop part connected to each other via connecting lines;

wherein the plasma separation/retransfusion loop part comprises a blood input pipe, a blood input peristaltic pump, a heparin pump, a plasma separation column, a first pressure monitor, and a heater connected in sequence via first connecting lines, wherein an exhaust pipe spring clamp is arranged on a connecting line between the blood input pipe and the blood input peristaltic pump; a blood inlet, a plasma outlet, and a blood cell outlet are arranged on the plasma separation column; and the blood inlet communicates with an outlet of the heparin pump; and the cell reactor/plasma component exchange double-loop part comprises a plasma input peristaltic pump, and a semipermeable membrane exchange column, a plasma exchange peristaltic pump, a red blood cell (RBC) pool, a membrane lung, the multilayer porous bioreactor, a second pressure monitor, and a third pressure monitor arranged in a 37° C. dedicated incubator and connected to the plasma outlet in sequence via second connecting lines, wherein a lower plasma inlet, a lower plasma outlet, an upper plasma inlet, and an upper plasma outlet are arranged on the semipermeable membrane exchange column; the lower plasma inlet communicates with an outlet of the plasma input peristaltic pump, and the lower plasma outlet communicates with an inlet of the plasma exchange peristaltic pump; wherein the multilayer porous bioreactor comprises a tank body, a tank cover, and a multilayer porous plate device; the tank cover is threadedly connected to an upper tank mouth of the tank body, and is further sealed by a rubber ring sleeved on the upper tank mouth; a cell input hole and a culture outlet pipe are arranged on an upper surface of the tank cover; a culture inlet pipe is arranged at a bottom of the tank body; the human iPSCs-derived HLCs are perfused into the tank body through the cell input hole; the cell input hole is equipped with a sealing cover; the membrane lung communicates with the culture inlet pipe via a connecting line; the second pressure monitor communicates with the culture outlet pipe via a connecting line; and the multilayer porous plate device is connected to an inner wall of the tank body in a manner such that the multilayer porous plate device slides up and down; wherein the multilayer porous plate device comprises at least one layer of a porous plate, and the porous plate comprises a plate, grooves, and bottom brackets; the grooves and the bottom brackets are circularly arranged on an upper surface and a lower surface of the plate at opposite positions, respectively; upper and lower adjacent layers of porous plates are removably connected by inserting the bottom brackets of an upper porous plate into the grooves of a lower porous plate; vertical hollowing holes are evenly distributed on a surface of the plate, and the vertical hollowing holes penetrate through the plate longitudinally; the bottom brackets are hollow cylinders; and horizontal hollowing holes are arranged on side walls of the bottom brackets; wherein the tank body has a diameter of 126 mm, a height of 160 mm, and a wall thickness of 4 mm; the multilayer porous plate device comprises 50 to 60 layers of porous plates; circular polycarbonate (PC) plates with a diameter of 120 mm and a thickness of 1 mm are used as the plates of the porous plates; and an outer surface of each of the circular PC plates is coated with a layer of growth factor and collagen; the second pressure monitor communicates with the upper plasma inlet and the upper plasma outlet communicates with the third pressure monitor; an outlet of the third pressure monitor and a blood cell outlet are connected to an inlet of the first pressure monitor; and an outlet of the first pressure monitor is connected to the heater and a blood output pipe in sequence.

2. The BAL according to claim 1, wherein the plasma separation column is a membrane plasma separator.

3. The BAL according to claim 2, wherein the semipermeable membrane exchange column is a membrane plasma component separator, and a semipermeable membrane of the semipermeable membrane exchange column has a pore size of 11 nm.

4. The BAL according to claim 3, wherein the RBC pool is a silicone rubber bag with 110 mL of RBCs; an inlet and an outlet are arranged at a front end and a rear end of the silicone rubber bag, respectively; and the inlet and the outlet are connected to the connecting lines.

5. The BAL according to claim 4, wherein the membrane lung is a membrane oxygenator.

6. The BAL according to claim 1, wherein the first connecting lines and the second connecting lines are made of medical grade polyvinyl chloride (PVC); and connecting lines connected to the blood input peristaltic pump and the plasma input peristaltic pump have an outer diameter of 13 mm, and other connecting lines have an outer diameter of 5.7 mm.

7. The BAL according to claim 1, wherein the grooves and the bottom brackets are circularly arranged respectively on the upper surface and the lower surface of the plate correspondingly in an inner ring and an outer ring, with 6, 8, or 11 grooves and bottom brackets in each ring; the grooves and bottom brackets are evenly distributed on a circumference around a center of the plate; the grooves are cylindrical grooves with a diameter of 11 mm and a depth of 0.8 mm; the bottom brackets are annular bottom brackets with a diameter of 11 mm and a height of 2 mm; and the vertical hollowing holes and the horizontal hollowing holes are circular holes with a diameter of 2 mm.

* * * * *